United States Patent [19]

Chan

[11] Patent Number: 4,675,316
[45] Date of Patent: Jun. 23, 1987

[54] SUBSTITUTED AZOYLMETHYLARYLSULFIDES AND DERIVATIVES AND PESTICIDAL USE THEREOF

[75] Inventor: Hak-Foon Chan, Doylestown, Pa.

[73] Assignee: Rohm and Haas Company, Philadelphia, Pa.

[21] Appl. No.: 885,237

[22] Filed: Mar. 10, 1978

[51] Int. Cl.$^4$ .................. A01N 43/50; A01N 43/653; C07D 233/60; C07D 249/08
[52] U.S. Cl. ..................................... 514/184; 514/383; 514/399; 548/101; 548/262; 548/341
[58] Field of Search ....................... 548/341, 101, 262; 260/299, 308 R; 424/269, 273 R, 245; 514/184, 383, 399

[56] References Cited

U.S. PATENT DOCUMENTS

| | | | |
|---|---|---|---|
| 3,444,175 | 5/1969 | Shen et al. | 548/341 |
| 3,551,444 | 12/1970 | Shen et al. | 548/341 |
| 3,746,768 | 7/1973 | Bordenca et al. | 548/341 |
| 3,821,394 | 6/1974 | Timmler et al. | 514/396 |
| 3,940,413 | 2/1976 | Kramer et al. | 548/341 |
| 4,005,083 | 1/1977 | Büchel et al. | 548/101 |
| 4,055,652 | 10/1977 | Walker | 424/273 R |
| 4,078,071 | 3/1978 | Walker | 548/341 |
| 4,085,209 | 4/1978 | Miller et al. | 548/341 |
| 4,394,380 | 7/1983 | Balasubramonyan et al. | 514/383 |

FOREIGN PATENT DOCUMENTS

| | | |
|---|---|---|
| 2640823 | 3/1977 | Fed. Rep. of Germany . |
| 1486817 | 6/1967 | France ............................. 548/341 |

OTHER PUBLICATIONS

Grant. ed. Hackh's Chemical Dictionary, McGraw-Hill, N.Y., 1972, pp. 75 and 428.
Baggaley et al., J. Chem. Soc., Perkin I, 1975, pp. 1670–1671.

Primary Examiner—Richard L. Raymond
Attorney, Agent, or Firm—Polly E. Ramstad

[57] ABSTRACT

This invention relates to substituted azoylmethylarylsulfides, sulfoxides and sulfones, their agronomically acceptable acid addition salts, their method of preparation and their pesticidal use, especially their use as highly active fungicides.

31 Claims, No Drawings

SUBSTITUTED AZOYLMETHYLARYLSULFIDES AND DERIVATIVES AND PESTICIDAL USE THEREOF

SUMMARY OF THE INVENTION

This invention relates to azolylmethylarylsulfides, sulfoxides and sulfones of the formula

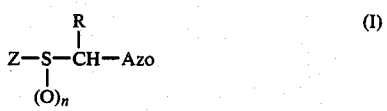

wherein Z is an aryl group; R is an alkyl group, a cycloalkyl group, an alkenyl group, a cycloalkenyl group, an alkynyl group, a cyano group, a cyanoalkyl group, a alkoxyalkyl group, an aryl group, an aryloxy group, an aryloxyalkyl group, an aryloxyarylalkyl group, an arylthio group, an arylthioalkyl group or an arylthioarylalkyl group; Azo is an imidazolyl group, a 1(H)-1,2,4-triazolyl group or a 4(H)-1,2,4-triazole group; n is zero or the integers one or two; and the agronomically acceptable acid addition salts and metal salt complexes thereof. This invention also relates to the method of preparation of these pesticidal agents, and in particular, to their use as highly active, broad spectrum, phytopathogenic fungicides.

DETAILED DESCRIPTION OF THE INVENTION

This invention relates to the substituted azolylmethylarylsulfides, sulfoxides and sulfones of Formula (I), above,
wherein:
Z is a ($C_6$ to $C_{10}$) optionally substituted aryl group;
R is
(a) a ($C_1$ to $C_{12}$) alkyl group;
(b) a ($C_3$ to $C_8$) cycloalkyl group;
(c) a ($C_2$ to $C_8$) alkenyl group;
(d) a ($C_5$ to $C_8$) cycloalkenyl group;
(e) a ($C_2$ to $C_8$) alkynyl group;
(f) a cyano group;
(g) a cyano ($C_1$ to $C_4$) alkyl group;
(h) a ($C_1$ to $C_6$) alkoxy ($C_1$ to $C_6$) alkyl group;
(i) a ($C_6$ to $C_{10}$) aryl group;
(j) a ($C_6$ to $C_{10}$) aryloxy group;
(k) a ($C_6$ to $C_{10}$) aryloxy ($C_1$ to $C_9$) alkyl group;
(l) a ($C_6$ to $C_{10}$) aryloxy ($C_6$ to $C_{10}$) aryl ($C_1$ to $C_9$) alkyl group;
(m) a ($C_6$ to $C_{10}$) arylthio group;
(n) a ($C_6$ to $C_{10}$) arylthio ($C_1$ to $C_9$) alkyl group; or
(o) a ($C_6$ to $C_{10}$) arylthio ($C_6$ to ($C_{10}$) aryl ($C_1$ to $C_9$) alkyl group;
Azo is an imidazolyl group, a 1(H)-1,2,4-triazolyl or 4(H)-1,2,4-triazolyl group;
n is zero or the integer one or two;
and the agronomically acceptable acid addition salts and metal salt complexes thereof.

In the definition of the substituents Z and R in the present specification and claims, the term "aryl" is meant to include both phenyl and naphthyl groups, preferably a phenyl group, either of which can be "optionally substituted" with up to three substituents, preferably with up to two substituents, selected from the group consisting of halogen, ($C_1$ to $C_4$) alkyl, ($C_1$ to $C_4$) alkoxy, trihalomethyl, nitro and cyano. The above terms "alkyl" and "alkoxy" encompass both branched and straight chain groups.

In the definition of the substituent R in the present specification and claims, the terms "alkyl, alkenyl, alkynyl and alkoxy" are also meant to encompass both branched and straight chain groups.

Among the agronomically acceptable acids which can be utilized in making the acid addition salts of this invention are hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, benzoic, phthalic and the like.

Among the agronomically acceptable metal salts having the Formula (MY) which can be utilized in making the metal salt complexes of this invention are metal salts wherein the metal cation(M) is selected from Groups IIA, IB, IIB, VIB, VIIB and VIII of the Periodic Table and the anion (Y) is a counterion selected in such a manner that the sum of the valence charges of the cation M and the anion X equals zero.

Typical cations(M) of the metal salt complexes of this invention are magnesium, manganese, copper, nickel, zinc, iron, cobalt, calcium, tin, cadmium, mercury, chromium, lead, barium and the like.

Typical anions (Y) of the metal salt complexes of this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) (di) ($C_1$ to $C_4$) alkyldithiocarbamate, ($C_1$ to $C_4$) alkylene-bis-dithiocarbamate and the like.

A preferred embodiment of this invention relates to compounds of Formula (I), above, wherein Z is an optionally substituted phenyl group; R is a ($C_1$ to $C_8$) alkyl group, a cyclohexyl group, an allyl group, a cyclohexenyl group, a propargyl group, a cyano group, a cyanomethyl or cyanoethyl group, a ($C_1$ to $C_4$) alkoxy ($C_1$ to $C_4$) alkyl group, or a phenyl, phenoxy, phenoxy ($C_1$ to $C_5$) alkyl, phenoxyphenyl ($C_1$ to $C_5$) alkyl, phenylthio, phenylthio ($C_1$ to $C_5$) alkyl and phenylthiophenyl ($C_1$ to $C_5$) alkyl group, the phenyl portions of which are optionally substituted with up to two substituents selected from the group consisting of halogen, ($C_1$–$C_4$) alkyl, ($C_1$–$C_4$) alkoxy, trihalomethyl, nitro and cyano; Azo is an imidazoyl or a 1(H)- or 4(H)-1,2,4-triazolyl group; n is zero or the integer one or two; and the agronomically acceptable acid addition salts and metal salt complexes thereof.

A more preferred embodiment of this invention is the compounds of Formula (I) above, wherein Z is a phenyl group optionally substituted with up to two halogen atoms, preferably chlorine atoms, R is a ($C_1$ to $C_4$) alkyl group, a phenyl group optionally substituted with up to two halogen atoms, preferably chlorine atoms, a phenoxy ($C_1$ to $C_5$) alkyl group the phenyl portion of which is optionally substituted with up to two halogen atoms preferably chlorine atoms; Azo is an imidazolyl, or a 1(H) or 4(H)-1,2,4-triazolyl group; n is zero, and the agronomically acceptable acid addition salts and metal salt complexes thereof.

The most preferred compounds encompassed by this invention are those wherein Z is phenyl or 4-chlorophenyl; R is ($C_1$ to $C_4$) alkyl, preferably n-butyl, dihalosubstituted phenyl, preferably 2,4-dichlorophenyl, or dihalosubstituted phenoxy ($C_1$ to $C_5$) alkyl, preferably 2,4-dichlorophenoxymethyl or 2,4-dichlorophenoxypentyl; Azo is an imidazolyl group; n is zero and the agronomically acceptable acid addition salts and metal salt complexes thereof.

Typical compounds encompassed by the present invention include:

1-[α-(2-chlorophenylthio)-2,3-dichlorobenzyl-]imidazole
1-[α-(3-chlorophenylsulfinyl)-3,4-dichlorobenzyl]1,2,4-triazole
1-[α-(4-chlorophenylsulfonyl)-3,5-dichlorobenzyl-]imidazole
4-[α-(2,3-dichlorophenylthio)-2,5-dichlorobenzyl]1,2,4-triazole
1-[α-(2,4-dibromophenylsulfinyl)-2,4-dibromobenzyl-]imidazole
1-[α-(2,5-difluorophenylsulfonyl)-2-chlorobenzyl]1,2,4-triazole
1-[α-(3,4-dibromophenylthio)-3-fluorobenzyl]imidazole
4-[α-(3,5-diiodophenylsulfinyl)-4-bromobenzyl]1,2,4-triazole
1-[1-(2,4,6-trichlorophenylsulfonyl)ethyl]imidazole
1-[1-(2,4,5-trichlorophenylthio)propyl]-1,2,4-triazole
1-[1-(2,3,5-trichlorophenylsulfinyl)butyl]imidazole
4-[1-(2,4,6-trimethylphenylsulfonyl)hexyl]-1,2,4-triazole
1-[1-(2,4,6-trifluorophenylthio)octyl]imidazole
1-[1-(2,4,6-trimethoxyphenylsulfinyl)nonyl]-1,2,4-triazole
1-{[1-(2,4-difluorophenylsulfonyl)-1-cyclohexyl]methyl}imidazole
1-{[1-(2,4-ditrifluoromethylphenylthio)-1-cyclohexnyl]-methyl}-1,2,4-triazole
1-[1-(3,4,5-trimethylphenylsulfinyl)-2-butenyl-]imidazole
1-[1-(2,4,6-trimethoxyphenylsulfonyl)-3-pentenyl]-1,2,4-triazole
1-[1-(3,5-dinitrophenylthio)-2-butynyl]imidazole
4-[1-(3,5-dicyanophenylsulfinyl)-3-pentynyl]-1,2,4-triazole
1-[1-cyano-1-(2-methyl-3,4-difluorophenylsulfonyl)methyl]imidazole
1-[2-cyano-1-(2-chloro-3,5-dibromophenylthio)ethyl]-1,2,4-triazole
1-[3-cyano-1-(2,4,5-trinitrophenylsulfinyl)propyl-]imidazole
4-{[1-(2,4-dichlorophenylsulfonyl)-4-butyloxy]butyl}-1,2,4-triazole
1-{[1-(2,4-difluorophenylthio)-2-methoxy]ethyl-}imidazole
1-{[1-(4-iodophenylsulfinyl)-1-ethoxy]methyl}-1,2,4-triazole
1-{[1-(2,5-dinitrophenylsulfonyl)-4-(2,4-dichlorophenoxy)]butyl}imidazole
4-{[1-(2,4-dicyanophenylthio)-1-(3,4-dichlorophenoxy)]methyl}-1,2,4-triazole
1-{[1-(3,4-dimethoxyphenylsulfinyl)-1-(4-chlorophenylthio)]methyl}imidazole
1-{[1-(2-nitro-3-methyl-4-chlorophenylsulfonyl)-1-(4-bromophenylthio)]methyl}-1,2,4-triazole
1-{[1-(2,5-ditrifluoromethylphenylthio)-4-(2,4-dichlorophenyl)]butyl}imidazole
and the like and the agronomically acceptable acid addition salts and metal salt complexes thereof.

The compounds of the present invention can be prepared by general synthetic routes. In particular, the compounds of the present invention can be prepared by the following reaction sequence. The isolation of the final products in each case is by the standard techniques of extraction, crystallization, distillation, chromotography and the like.

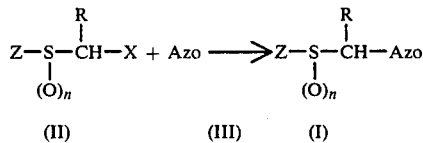

Arylalkyl sulfides, or derivatives thereof such as the sulfoxides or sulfones of Formula II, wherein (X) is a suitable leaving group such as a halide, aryl or alkylsulfonates and the like, are reacted with an imidazole, a triazole, or an imidazole or triazole metal salt, either neat or in an appropriate solvent such as dimethyl sulfoxide, dimethylformamide and the like, at temperatures from about 50° C. to about 200° C. to give the compounds of Formula I.

The starting materials of Formula II can be obtained by various synthetic routes well-known in the art. For example, the compounds of Formula (II) can be prepared by the following reaction sequence.

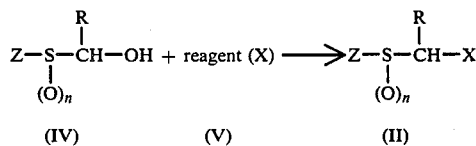

The compounds of Formula IV are reacted with a leaving group reagent (X) such as thionyl chloride or bromide, methane sulfonyl chloride, p-toluenesulfonyl chloride, N-chloro or N-bromosuccinimide and the like either neat or in a suitable solvent such as benzene, toluene, carbon tetrachloride, chloroform, methylene chloride, diethyl ether and the like at temperatures from about 0° C. to about 100° C. to give the compounds of Formula II.

The compounds of Formula II can be prepared by well-known synthetic routes such as the following reaction sequence.

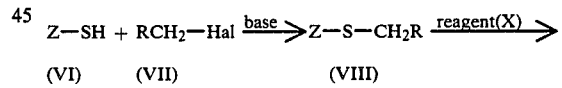

The arylmercaptans of Formula VI are reacted with a substituted alkyl halide of Formula VII wherein Hal is a halide, preferably a chloride or bromide in an aqueous medium in the presence of a strong base such as sodium hydroxide, potassium hydroxide and the like at temperatures from about room temperature to about 150° C. to give the compounds of Formula VIII. These compounds are reacted with a leaving group reagent (X) using the conditions stated above to give the compounds of Formula II, n=o.

The compounds of Formula II, n=o can either be carried through the first reaction sequence as the sulfide to give the product of Formula I where n=o and then oxidized to the sulfoxide or sulfone product of Formula I, n=1 or 2, or it can be oxidized first to the sulfoxide or sulfone of Formula II, n=1 or 2, and then carried through the first sequence to the product of Formula I where n=1 or 2.

In the oxidation of the sulfide to the sulfoxide or sulfone, the sulfide is dissolved in an appropriate nonoxidizable solvent such as methylene chloride, carbon tetrachloride and the like and is then treated with an oxidizing agent such as meta-chloroperbenzoic acid, peracetic acid, hydrogen peroxide, and the like at temperatures from about −15° C. to about 80° C. If the sulfoxide is desired a one to one molar ratio of sulfide to peracid or peroxide is used. If the sulfone is desired a one to two or more molar ratio of sulfide to peracid or peroxide is utilized.

The acid addition salts of the compounds of the present invention can be prepared by standard techniques well-known in the art. For example, the compounds of Formula I can be dissolved in an appropriate solvent such as diethyl ether, tetrahydrofuran, ethanol, methanol and the like or combinations thereof, and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the compounds of the present invention can be prepared by adding dropwise, with stirring, a stoichiometric amount of a metal salt dissolved in an appropriate solvent or combination of solvents to a solution of the compounds according to Formula I dissolved in a similarly appropriate solvent or combination of solvents. The reaction mixture is briefly stirred and the solvent is removed under reduced pressure to give the respective metal salt complex.

The metal salt complexes can also be prepared by mixing stoichiometric or excess amounts of the metal salt and a compound according to Formula I in the desired amount of solvent containing appropriate adjuvants just prior to spraying the plants. Adjuvants that may be included in the "in-situ" preparation may be detergents, emulsifiers, wetting agents, spreading agents, dispersing agents, stickers, adhesives, and the like which are used in agricultural applications.

Solvents that can be utilized in these procedures include any polar solvent e.g., water, methanol, ethanol, isopropanol, or ethylene glycol and any aprotic dipolar solvent, e.g., dimethylsulfoxide, acetonitrile, dimethylformamide, nitromethane or acetone, or any combination thereof.

The metal salt cations that can be used in these procedures can be selected from the group consisting of calcium, magnesium, manganese, copper, nickel, zinc, iron, cobalt, tin, cadmium, mercury, chromium, lead, barium, and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate, tartarate, maleate, and the like may be utilized as the counterion in the metal salt.

Any metal containing fungicides can also be used in place of metal salts. Typical metal containing fungicides that can be utilized in these procedures are: (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); (b) copper-based fungicides such as cuprous oxide, copper oxychloride, copper naphthenate, and Bordeaux mixture; and (c) miscellaneous fungicides such as: phenylmercuri acetate, N-ethyl-mercuri-3,4,5,6,7,7-hexachlorophthalimide, phenylmercuri monoethanolammonium lactate, nickel-containing compounds and calcium cyanamide.

The compounds of this invention possess an assymetric carbon atom and thus exist as racemic mixtures. The d and l enantiomorphs in these racemic mixtures can be separated via standard techniques such as fractional crystallization with d-tartaric acid, l-tartaric acid, l-quinic acid and the like, followed by basification and extraction of the d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 1

Preparation of 1-[1-(4-chlorophenylthio)pentyl]imidazole

A. p-chlorophenyl pentyl sulfide

To a solution of 8.0 g (0.2 mole) of sodium hydroxide in 100 ml of water is added 29 g (0.2 mole) of p-chlorothiophenol in small portions. Stirring is continued until the mixture becomes clear. To this solution is added 30.2 g (0.2 mole) of pentyl bromide dropwise. The reaction mixture is heated at 60° C. for one hour. It is then poured into water and extracted with ether. The combined ether extracts are washed with water and dried over MgSO$_4$. Solvent is evaporated to give a pale yellow oil which is purified further by vacuum distillation (85°–8°/0.03 mm) to give 15 g of pure product.

B. p-Chlorophenyl-α-chloropentyl sulfide

To a solution of 12.6 g (0.06 mole) of p-chlorophenyl pentyl sulfide in 50 ml of methylene chloride is added 8.3 g (0.06 mole) of sulfuryl chloride dropwise over a period of one hour. The reaction is stirred at room temperature overnight. Solvent is evaporated under vacuum to give 16 g of crude product.

1-[1-(4-Chlorophenylthio)pentyl]imidazole

A mixture of 5 g p-chlorophenyl-α-chloropentyl sulfide and 5 g of imidazole is heated at 100° for two hours. The reaction mixture is poured into water and extracted with ether. The combined ether extracts are washed with water and dried over MgSO$_4$. Drying agents are filtered and dry hydrogen chloride gas is bubbled into the ether solution. Oily precipitate separates from the solution and is back neutralized with 10% ammonium hydroxide to give 4 g of a yellow oil.

nmr (CDCl$_3$): δ 0.8–2.4 (m, 9H), 5.1 (t, 1H), 6.9–7.5 (m, 7H)

EXAMPLE 5

Preparation of 1-[α-(4-chlorophenylthio)-2,4-dichlorobenzyl-]imidazole

A. 4-Chlorophenyl-2,4-dichlorobenzyl sulfide

A 10% sodium hydroxide solution is prepared by dissolving 10.4 g (0.26 mole) of NaOH in 100 ml of water. To this solution is added 36 g (0.25 mole) of 4-chloro-thiophenol. The mixture is heated over a steam bath for ½ hour. A solution of 50 g (0.26 mole) of α 2,4-trichlorotoluene is then added dropwise with stirring. The reaction mixture is heated at 80° overnight. It is then cooled and poured into water and extracted with ether. The combined ether extracts are washed with water and dried over MgSO$_4$. Solvent is evaporated to give 78.6 g of crude product. Vacuum distillation (150°–170°/0.02 mm) afforded 60 g (79%) of pure product, m.p. 54°–7°.

B. 4-Chlorophenyl-α-chloro-2,4-dichlorobenzyl sulfide

A solution of 6.75 g (0.05 m) of sulfuryl chloride in 50 ml of methylene chloride is added dropwise to a solution of 15 g (0.05 m) of 4-chlorophenyl-2,4-dichlorobenzyl sulfide in 50 ml of methylene chloride at room temperature. The resulting solution is stirred at r. t. overnight. Solvent and excess sulfuryl chloride is evaporated under vacuum to give 16.6 g of a yellow oil. This material is used for the next experiment without further purification.

C.
1-[α-4-chlorophenylthio)-2,4-dichlorobenzyl]imidazole

A mixture of 8.6 g of 4-chlorophenyl-α-chloro-2,4-dichlorobenzyl sulfide and 8 g of imidazole is heated at 130° for 3 hours. The reaction mixture is poured into water and extracted with ether. The combined ether extracts are washed with water and dried over MgSO$_4$. The drying agent is filtered and the product is purified by converting it to its hydrochloride salt and then back neutralizing it with dilute NH$_4$OH solution to give 8 g of a brown oil.

nmr (CDCl$_3$): δ 6.7 (S, 1H), 6.8–7.7 (m, 10H)

EXAMPLE 6

Preparation of nitric acid salt of
1-[α-(4-chlorophenylsulfinyl)-2,4-dichlorobenzyl-]imidazole To a solution of 5 g (0.014 m) of 1[α-(4-chlorophenylthio)2,4-dichlorobenzyl]imidazole in 10 ml of methylene chloride is added in portions 2.84 g (0.014 m) of m-chloroperoxybenzoic acid at 0°. The reaction mixture is then stirred at r. t. overnight. Conc. nitric acid is added dropwise to this solution until it is acidic followed by 150 ml of anhydrous ether. Solid formed is then collected by filtration to give 3.3 g of a white solid, m.p. 138°–40°.

EXAMPLE 8

Preparation of
1-[α-(4-chlorophenylsulfonyl)-2,4-dichlorobenzyl-]imidazolium nitrate To a solution of 5 g (0.013 mole) of 1[α-(4-chlorophenylsulfinyl)-2,4-dichlorobenzyl]imidazole dissolved in 50 ml of methylene chloride is added 2.7 g (0.013 mole) of m-chloroperoxybenzoic acid in small portions at 0°. The reaction mixture is stirred at room temperature overnight. Concentrated nitric acid is added dropwise until the solution becomes acidic. When the reaction mixture is diluted with anhydrous ether, a white precipitate forms which is collected by filtration to give 4 g of desired product, mp 149°–9° (dec.).

nmr (DMSO): δ 7.5–8.6 (m, 11H), 12.8 (S, 1H)

EXAMPLE 10

Preparation of
1-(Cyano-p-chlorophenylthiomethyl)imidazoles

A. α-Chloro-α-p-chlorophenylthioacetonitrile

Into a 500 ml four-necked round bottom flask equipped with a stirrer, a thermometer, and a condenser, are placed 300 ml of carbon tetrachloride and 55 g (0.3 mole) of p-chlorophenylthioacetonitrile. To this mixture is added 40 g (0.3 mole) of N-chlorosuccinimide in small portions. The reaction mixture is stirred at room temperature overnight. The white solid which forms is filtered and the filtrate is concentrated under vacuum to give 6.95 g of desired product.

B. 1-(Cyano-p-chlorophenylthiomethyl)imidazole

Into a 125 ml three-necked round bottom flask are placed 33 g (0.15 mole) of α-chloro-α-p-chlorophenylthioacetonitrile and 33 g (0.48 mole) of imidazole. The mixture is heated to 60° when an exothermic reaction sets in (110°). It is then cooled to room temperature, poured into water and extracted with ether. The combined ether extracts are evaporated to give 20 g of a brown solid which when triturated with ether gives 7 g of pure product, mp 120°–2°.

nmr (CDCl$_3$): δ 6.2 (S, 1H), 7.0–7.5 (m, 7H)

EXAMPLE 19

Preparation of
1-[1-(p-chlorophenylthio)-2-(2,4-dichlorophenoxy)hexyl]imidazole

A. 1-(p-chlorophenylthio)hexan-2-ol

To 28.9 g (0.2 mole) the p-chlorothiophenol and 8.0 g (0.2 mole) of sodium hydroxide in 100 ml of water is added 22.0 g (0.22 mole) of 1,2-epoxyhexane over 10 minutes. When addition is completed, the mixture is heated to reflux for 16 hours. The mixture is cooled, combined with 300 ml of water and the organic phase is separated.

The aqueous phase is extracted with ether (2×75 ml), and the extract is combined with the organic phase, washed with water and the solution is dried over anhydrous sodium sulfate. The ether is stripped to give 46.4 g (94.8%) crude product. Distillation (123°–5° C./0.1 mm) provided 42.0 g of pure product.

B. 1-(p-chlorophenylthio)hex-2-yl methane sulfonate

To 42.0 g (0.172 mole) of 1-(p-chlorophenylthio)hexan-2-ol and 21.6 g (0.189 mole) of methane sulfonyl chloride in 100 ml of toluene is slowly added 20.8 g (0.206 mole) of triethylamine over a ½ hour period at less than 15° C. When the addition is completed, the mixture is stirred for ½ hour, and is allowed to warm to ambient temperature.

The mixture is then warmed to 60° C. for one hour, cooled, and the solids are filtered. The filtrate is washed with water, dried over anhydrous sodium sulfate, and concentrated to give 49.1 g (88.6%) of the crude mesylate product.

C.
1-(p-chlorophenylthio)-2-(2,4-dichlorophenoxy)hexane

To 10.6 g (0.065 mole) of 2,4-dichlorophenol in 125 ml of dimethyl sulfoxide (DMSO) is added 2.6 g (0.065 mole) of sodium hydroxide and the mixture is heated to 100° with a solution forming. This solution is placed under house vacuum (30–50 mm) and 40 ml of DMSO-H₂O is distilled.

The solution is cooled, and to it is added 19.8 g (0.0613 mole) of 1-(p-chlorophenylthio)hex-2-yl methane sulfonate. This mixture is stirred for one hour at 60° C., and then it is cooled and combined with 200 ml of water. The organic material is extracted with 2×100 ml of ether, and the extract is dried over anhydrous sodium sulfate, and the ether is distilled to give 24.2 g of crude product. Material is distilled at 148° C./0.25 mm leaving 10.4 g of more pure product.

D.
1-Chloro-1-(p-chlorophenylthio)-2-(2,4-dichlorophenoxy)hexane

To 10.4 g (0.0267 mole) of 1-(p-chlorophenylthio)-2-(2,4-dichlorophenoxy)hexane in 75 ml of methylene chloride is slowly added dropwise 3.6 g (0.0267 mole) of sulfuryl chloride in 75 ml of methylene chloride over a 4 hour period. When the addition is complete, the reaction is stirred at ambient temperature for several hours before it is stripped to dryness to give 9.6 g of the crude chloride.

E.
1-[1(p-chlorophenylthio)-2-(2,4-dichlorophenoxy)hexyl]imidazole

To 9.6 g of the crude 1-chloro-1-(p-chlorophenylthio)-2-(2,4-dichlorophenoxy)hexane is added 10.0 g (0.147 mole) of imidazole and the mixture is heated to 90° C. for four hours. The reaction is cooled, and diluted with water. The organic material is extracted 2×75 ml of ehter, and the extract is dried over anhydrous sodium sulfate.

The ether solution is treated with dry hydrogen chloride, and the oil which settles is separated by decanting the ether solution to give 2.6 g of dark residue. This oil is treated with dilute ammonium hydroxide and organic material is extracted with ether. The extract is dried over anhydrous sodium sulfate and concentrated to give 2.3 g of the crude product.

EXAMPLE 2
Preparation of 1-[(1-phenylthio-3-cyano)propyl]1,2,4-triazole

A. 4-Chloro-4-phenylthiobutyronitrile

To a solution of 50 g (0.28 mole) of 4-phenylthiobutyronitrile in 200 ml of methylene chloride is added 40.5 g (0.3 mole) of sulfuryl chloride dropwise during a period of six hours. Stirring is continued overnight. Solvent and excess sulfuryl chloride is then evaporated under vacuum to give 61 g of a crude product. This material is used in the next experiment without further purification.

B. 1-[(1-Phenylthio-3-cyano)propyl]1,2,4-triazole

A mixture of 20 g of 4-chloro-4-phenylthiobutyronitrile and 20 g of 1(H)-1,2,4-triazole is mixed and heated at 100° overnight. The reaction mixture is cooled, poured into water and extracted with ether. The combined ether extracts are washed with water and dried over MgSO₄. The free base is further purified by converting it to its hydrochloride salt and back neutralizing it with dilute ammonium hydroxide solution. A total of 7 g of off white solid (m.p. 70°–2°) is obtained.

nmr (CDCl₃): δ2.4–2.7 (m, 4H), 5.6 (t, 1H), 7.3 (S, 5H), 7.8 (S, 1H), 7.9 (S, 1H).

Tables I and II give the structure, melting points in degrees centigrade and the elemental analysis of some of the more representative compounds encompassed by the present invention which were synthesized by the above procedures.

TABLE I

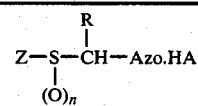

| Ex. No. | Z | R | n | Azo | HA |
|---|---|---|---|---|---|
| 1 | 4-ClC₆H₄ | C₄H₉—n | 0 | imidazole | — |
| 2 | 4-ClC₆H₄ | C₄H₉—n | 1 | imidazole | — |
| 3 | C₆H₅ | CH₂CN | 0 | imidazole | — |
| 4 | C₆H₅ | CH₂CH₂CN | 0 | imidazole | — |
| 5 | 4-ClC₆H₄ | 2,4-Cl₂C₆H₃ | 0 | imidazole | — |
| 6 | 4-ClC₆H₄ | 2,4-Cl₂C₆H₃ | 1 | imidazole | HNO₃ |
| 7 | 4-ClC₆H₄ | 2,4-Cl₂C₆H₃ | 1 | imidazole | — |
| 8 | 4-ClC₆H₄ | 2,4-Cl₂C₆H₃ | 2 | imidazole | HNO₃ |
| 9 | C₆H₅ | CN | 0 | imidazole | HCl |
| 10 | 4-ClC₆H₄ | CN | 0 | imidazole | — |
| 11 | 4-ClC₆H₄ | CN | 0 | imidazole | HNO₃ |
| 12 | 4-ClC₆H₄ | CN | 1 | imidazole | HNO₃ |
| 13 | 4-ClC₆H₄ | CH₂CN | 0 | imidazole | HCl |
| 14 | 4-ClC₆H₄ | CH₂CN | 1 | imidazole | — |
| 15 | 4-ClC₆H₄ | CH₂CN | 2 | imidazole | — |
| 16 | 4-ClC₆H₄ | 2,4-Cl₂C₆H₃OCH₂ | 0 | imidazole | HNO₃ |
| 17 | 4-ClC₆H₄ | 2,4-Cl₂C₆H₃OCH₂ | 0 | imidazole | — |
| 18 | 4-ClC₆H₄ | 2,4-Cl₂C₆H₃OCH₂ | 1 | imidazole | — |
| 19 | 4-ClC₆H₄ | 2,4-Cl₂C₆H₃OCH(C₄H₉) | 0 | imidazole | — |
| 20 | 4-ClC₆H₄ | 2,4-Cl₂C₆H₃OCH(C₄H₉) | 1 | imidazole | — |
| 21 | 4-ClC₆H₄ | CN | 0 | 1-triazole | HCl |
| 22 | C₆H₅ | CH₂CH₂CN | 0 | 1-triazole | — |
| 23 | 4-ClC₆H₄ | C₄H₉—n | 1 | 1-triazole | HNO₃ |
| 24 | 4-ClC₆H₄ | 2,4-Cl₂C₆H₃ | 0 | 1-triazole | — |
| 25 | 4-ClC₆H₄ | 2,4-Cl₂C₆H₃ | 0 | 1-triazole | HCl |
| 26 | 4-ClC₆H₄ | 2,4-Cl₂C₆H₃ | 1 | 1-triazole | HNO₃ |
| 27 | C₆H₅ | C₆H₅ | 0 | 1-triazole | HNO₃ |
| 28 | 4-ClC₆H₄ | 2,4-Cl₂C₆H₃OCH₂ | 0 | 1 & 4-triazole | — |

TABLE II

| Ex. No. | mp | Elemental Analysis: Calc'd (Found) | | | | | |
|---|---|---|---|---|---|---|---|
| | | C | H | Cl | N | O | S |
| 1 | oil | 59.88 | 6.10 | 12.62 | 9.98 | — | 11.42 |
| | | (59.83) | (6.18) | (13.15) | (9.92) | — | (11.61) |
| 2 | oil | 56.65 | 5.77 | 11.94 | 9.44 | 5.39 | 10.80 |
| | | (58.03) | (5.46) | (12.40) | (8.95) | (5.35) | (10.15) |
| 3 | oil | 62.86 | 4.84 | — | 18.32 | — | 13.98 |
| | | (62.44) | (4.43) | — | (17.44) | — | (14.52) |
| 4 | oil | 64.17 | 5.39 | — | 17.27 | — | 13.18 |
| | | (64.25) | (5.49) | — | (16.96) | — | (13.21) |
| 5 | oil | 51.98 | 3.00 | 28.77 | 7.58 | — | 8.67 |
| | | (52.00) | (3.10) | (28.91) | (7.99) | — | (8.42) |
| 6 | 138–40 | 42.83 | 2.69 | 23.70 | 9.36 | — | 7.15 |
| | | (42.39) | (2.62) | (23.51) | (10.04) | — | (6.88) |
| 7 | 129–32 | 49.82 | 2.87 | 27.58 | 7.26 | 4.15 | 8.32 |
| | | (50.02) | (2.95) | (27.09) | (7.55) | (4.46) | (8.62) |
| 8 | 145–9 | 41.35 | 2.60 | 22.89 | 9.04 | 17.21 | 6.90 |
| | | (41.63) | (2.74) | (22.31) | (9.90) | (16.70) | (6.68) |
| 9 | 138–40 | 52.48 | 4.00 | 14.08 | 16.69 | — | 12.74 |
| | | (52.02) | (4.10) | (15.01) | (16.59) | — | (12.61) |
| 10 | 120–2 (dec) | 52.91 (53.32) | 3.23 (3.23) | 14.20 (14.14) | 16.83 (17.05) | — — | 12.84 (13.12) |
| 11 | 105–8 | 39.94 | 3.02 | 11.79 | 18.63 | 15.96 | 10.66 |
| | | (40.52) | (3.02) | (11.42) | (19.07) | (16.25) | (9.34) |
| 12 | 92–3 (dec) | 40.19 (40.14) | 2.76 (2.93) | 10.78 (10.97) | 17.04 (16.64) | 19.47 (19.23) | 9.75 (9.81) |
| 13 | 177–9 | 48.01 | 3.69 | 23.62 | 14.00 | — | 10.68 |
| | | (47.72) | (3.64) | (23.55) | (14.16) | — | (10.88) |
| 14 | 121–3 | 51.52 | 3.60 | 12.67 | 15.02 | 5.72 | 11.46 |
| | | (50.74) | (3.47) | (13.01) | (14.64) | (6.66) | (11.46) |
| 15 | 153–5 | 48.74 | 3.41 | 11.99 | 14.21 | 10.82 | 10.84 |
| | | (48.35) | (3.33) | (13.03) | (13.90) | (11.00) | (10.90) |
| 16 | 98–100 | 44.13 | 3.05 | 22.99 | 9.08 | 13.83 | 6.92 |
| | | (42.17) | (3.24) | (19.80) | (11.87) | (16.84) | (6.49) |

TABLE II-continued

| Ex. No. | mp | Elemental Analysis: Calc'd (Found) | | | | | |
|---|---|---|---|---|---|---|---|
| | | C | H | Cl | N | O | S |
| 17 | oil | 51.08 | 3.28 | 26.61 | 7.01 | 4.00 | 8.02 |
| | | (52.75) | (3.55) | (23.80) | (7.10) | (3.72) | (10.46) |
| 18 | oil | 49.11 | 3.15 | 25.59 | 6.74 | 7.70 | 7.71 |
| | | (49.53) | (3.50) | (25.73) | (6.69) | (7.50) | (7.61) |
| 19 | oil | 55.33 | 4.64 | 23.33 | 6.15 | 3.51 | 7.03 |
| | | (56.04) | (4.65) | (22.58) | (6.93) | (4.19) | (7.10) |
| 20 | oil | 53.46 | 4.49 | 22.54 | 5.94 | 6.78 | 6.79 |
| | | (52.48) | (4.63) | (22.45) | (4.91) | (7.97) | (7.11) |
| 21 | 155-6 (dec) | 41.83 | 2.81 | 24.69 | 19.51 | — | 11.17 |
| | | (41.02) | (2.72) | (24.83) | (19.58) | | (11.10) |
| 22 | 70-2 | 58.99 | 4.95 | — | 22.93 | — | 13.12 |
| | | (58.55) | (4.91) | | (23.08) | | (12.98) |
| 23 | 110-5 | 43.27 | 4.75 | 9.83 | 15.53 | 17.74 | 8.89 |
| | | (43.57) | (4.68) | (10.73) | (14.78) | (17.59) | (9.14) |
| 24 | 130-1 | 48.60 | 2.72 | 28.69 | 11.34 | — | 8.65 |
| | | (48.30) | (265) | (28.72) | (11.49) | | (8.73) |
| 25 | 158-60 | 44.25 | 2.72 | 34.84 | 10.32 | — | 7.88 |
| | | (43.69) | (2.65) | (34.10) | (11.03) | | (7.58) |
| 26 | 120-3 | 40.06 | 2.47 | 23.65 | 12.46 | — | 7.13 |
| | | (39.77) | (2.55) | (23.07) | (12.32) | | (7.35) |
| 27 | 107-9 | 54.53 | 4.27 | — | 16.96 | 14.53 | 9.71 |
| | | (54.04) | (4.33) | | (16.91) | (14.94) | (9.80) |
| 28 | oil | 47.96 | 3.02 | 26.55 | 10.49 | 3.99 | 7.99 |
| | | (48.92) | (3.25) | (25.00) | (10.24) | (4.75) | (9.35) |

The azolylmethylarylsulfides, sulfoxides and sulfones, the acid addition salts and metal salt complexes of this invention are broad-spectrum fungicides which possess a high degree of activity against assorted phytopathogenic fungi. These compounds, salts and complexes are particularly effective at rates of application from about 50 to about 2000 ppm in controlling barley net blotch (*Helminthosporium teres*) on barley plants, chocolate spot (*Botrytis fabae*) on broad bean plants, bean powdery mildew (*Erysiphe polygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated, to spray these plants on a moving belt with the chemical agent and allow them to dry. The proper plants are then inoculated with the fungal spores and then allowed to incubate until the disease has developed and the percent control is read or estimated.

The following test methods are employed in evaluating the fungicidal activity of the compounds, salts and complexes of this invention.

EXAMPLE A

Barley Net Blotch (*Helminthosporium teres*)

Barley plants (var. Wong) are trimmed to a height of approximately 2.5 inches, 24 hours prior to chemical application. This procedure provides plants of a uniform height and permits rapid inoculation of treated plants. The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greenhouse at 70°-75° F. Treatment comparisons are made 6 to 7 days after inoculation. Typical barley net blotch symptoms initially appear as irregular sunken water-soaked areas which become necrotic as the lesions enlarge. Certain of the preferred compounds of this invention demonstrate complete control over *Helminthosporium teres* at application rates of 300 ppm.

EXAMPLE B

Broad Bean Chocolate Spot (*Botrytis fabae*)

*Botrytis fabae* is cultured on oatmeal agar (OA) slants for 21 days at ambient temperature and low light intensity. Spores are harvested by adding deionized water to the OA slants and scraping the agar surface with a rubber policeman or similar blunt object. The spore suspension is filtered through cheesecloth to remove mycelial and agar fragments and then adjusted to a concentration of 175-200,000 spores per ml with an inoculation media. The inoculation medium (20 gms glucose, 1 gm ammonium phosphate, 2 gm potassium nitrate, 10 mgs ascorbic acid, 1500 ml deionized water and 500 ml apple juice) is to provide improved spore germination on the surface of the broad bean leaves and stems. Broad bean plants are inoculated by spraying the foliage. Inoculated plants are incubated in a humid environment at 75°-85° F. for 66 hours. Treatment comparisons are made 66-68 hours after inoculation. Typical broad bean gray mold leaf spot symptoms appear as regular circular to lanceolate lesions on plant leaves and stems. Certain of the preferred compounds of this invention demonstrate greater than 90% control over *Botrytis fabae* at application rates of 300 ppm.

EXAMPLE C

Bean Powdery Mildew (*Erysiphe polygoni*)

Bean plants (var. Dwarf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface. Certain of the preferred compounds of this invention demonstrate complete control over *Erysiphe polygoni* at application rates greater than 300 ppm.

EXAMPLE D

Grape Downy Mildew (*Plasmopora viticola*) (GDM)

Grape seedlings (var. Siebel 1000) 4-5 inches tall are used. *Plasmopora viticola* is cultured on grape leaves for 7 days at 65°-75° F. in a growth room at moderate light intensity, and then placed into a 70°-75° humidity cabinet for 24 hours to obtain abundant sporulation on the undersurface of the grape leaves. Leaves containing heavy levels of downy mildew infection are harvested and placed into a widemouth screwtop quart jar or similar container. Deionized water is added to the container and the container is shaken to free the spores. The resulting spore suspension is filtered through cheesecloth to remove plant debris and adjusted to a concentration of 100-125,000 spores per ml. The grape plants are inoculated by spraying the leaves with a hand held air brush until small uniform droplets of inoculum are observed on the leaves. The inoculated plants are incubated in a humid environment at 65°-70° F. for 48 hours prior to being placed in a growth room. Treatment comparisons are made 7 days after inoculation. Typical grape downy mildew symptoms appear on the upper leaf surface as pale-yellow spots variable in size and form, frequently circular without a distinct line of demarcation. Under humid conditions the lower leaf surface is covered by conspicuous fungal growth. Certain of the preferred compounds of this invention possess complete control over *Plasmopora viticola* at application rates of 300 ppm.

EXAMPLE E

Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°–85° F.) for 24 hours prior to being placed in a greenhouse environment. Treatment comparisons are made 7 to 8 days after inoculation. Initial rice blast lesions appear as small brown necrotic spots on the foliage. The typical lesion is ecliptical, 1 to 2 cm. long with a large necrotic gray center and brown margins. Certain of the preferred compounds of this invention possess complete control over *Piricularia oryzae* at application rates of 300 ppm.

EXAMPLE F

Tomato Late Blight (*Phytophthora infestans*)

Tomato (var. Rutgers) seedlings, 2.5–3 inches tall, are fertilized with a water soluble fertilizer 4 to 5 days prior to chemical application to promote rapid succulent growth and better symptom expression. The spore suspension is applied with a DeVilbiss atomizer at 8 to 10 psi air pressure onto the leaf undersurface until fine droplets are formed. Inoculated seedlings are placed in a humid environment at 60°–62° F. for 40 to 45 hours, prior to being placed in the greenhouse at 70°–75° F. Treatment comparison are made 5 to 6 days after inoculation. Initially, typical tomato late blight symptoms appear as irregular, greenish-black, water-soaked patches which enlarge and become brown, with a firm corrugated surface. Severe infection will resemble frost damage. Certain of the preferred compounds of the present invention possess complete control over *Phytophthora infestans* at application rates of 300 ppm.

EXAMPLE G

Wheat Stem Rust (*Puccinia graminis* f. sp. *tritici* race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat steam rust is characterized by brick red spores in irregularly shaped sori on the leaves and stems of the wheat seedlings. Certain of the preferred compounds of the present invention possess complete control over *Puccinia graminis* f. sp. *tritici* race 15B-2 at application rates of 300 ppm.

The azoylmethylarylsulfides, sulfoxides and sulfones, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in an agronomically acceptable carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with an agronomically acceptable liquid or solid carrier and, when desired, suitable surfactants are incorporated.

By the term "agronomically acceptable carrier" is meant any substance which can be utilized to dissolve, disperse, or diffuse the chemical agent incorporated therein without impairing the effectiveness of the chemical agent and which does no permanent damage to such environment as the soil, the equipment and the agronomic crops.

It is usually desirable, particularly in the case of foliar spray formulations, to include adjuvants, such as wetting agents, spreading agents, dispersing agents, stickers, adhesives and the like in accordance with the agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compounds with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[1-(p-chlorophenylthio)-2-(2,4-dichlorophenoxy)hexyl-]imidazole, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the azoylmethylarylsulfides, sulfoxides and sulfones, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingrediet are commonly made and are subsequently diluted to from about 1% to about 10% use concentration.

The compounds, salts and complexes of this invention can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl)phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole,5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl, 2-(4'-thiazolyl)benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide-2,3-dihydro-5-carboxanili-do-6-methyl-1,4-oxathiin,α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine(ethirimol), acetate of 4-cyclododecyl-2,6-dimethylmorpholine (dodemorph), and 6-methyl-2-oxo-1,3-dithiolo[4,5-b]-quinoxaline (quinomethionate).

(d) miscellaneous halogenated fungicides such as: tetrachloro-p-benzoquinone (chloranil), 2,3-dichloro-1,4-naphthoquinone (dichlone), 2,3-dichloro-2,5-dimethoxybenzene (chloroneb), 3,5,6-trichloro-o-anisic acid (tricamba), 2,4,5,6-tetrachloroisophthalo nitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzenediazo sodium sulfonate, methyl isothiacyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido)benzene(thiophanatemethyl).

The compounds, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the compounds of this invention will suggest themselves to those skilled in the art of agriculture and horticulture.

I claim:

1. A compound of the formula

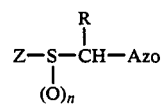

wherein

Z is a phenyl or naphthyl group optionally substituted with up to three substituents selected from the group consisting of halogen, $(C_1-C_4)$alkyl, $(C_1-C_4)$alkoxy, trihalomethyl, nitro and cyano;

R is
(a) $(C_1-C_{12})$alkyl;
(b) $(C_3-C_8)$cycloalkyl;
(c) $(C_2-C_8)$alkenyl;
(d) $(C_5-C_8)$cycloalkenyl;
(e) $(C_2-C_8)$alkynyl;
(f) cyano;
(g) cyano$(C_1-C_4)$alkyl;
(h) $(C_1-C_6)$alkoxy $(C_1-C_6)$alkyl;

(i) phenyl or naphthyl;
(j) phenoxy or naphthoxy;
(k) phenoxy ($C_1$-$C_9$)alkyl or naphthyloxy ($C_1$-$C_9$)alkyl;
(l) phenoxyphenyl ($C_1$-$C_9$)alkyl, phenoxynaphthyl ($C_1$-$C_9$)alkyl, naphthoxynaphthyl ($C_1$-$C_9$)alkyl or naphthoxyphenyl ($C_1$-$C_9$)alkyl;
(m) phenylthio or naphthylthio;
(n) phenylthio ($C_1$-$C_9$)alkyl or naphthylthio ($C_1$-$C_9$)alkyl; or
(o) phenylthiophenyl ($C_1$-$C_9$)alkyl, phenylthionaphthyl ($C_1$-$C_9$)alkyl, naphthylthiophenyl ($C_1$-$C_9$)alkyl or naphthylthionaphthyl ($C_1$-$C_9$)alkyl;

wherein when R is substituent of (i), (j), (k), (l), (m), (n) or (o), the phenyl or naphthyl moiety of such substituent may be optionally substituted with up to three substituents selected from the group consisting of halogen, ($C_1$-$C_4$)alkyl, ($C_1$-$C_4$)alkoxy, trihalomethyl, nitro and cyano;

Azo is 1(H)-imidazolyl or 1(H)- or 4(H)- 1,2,4-triazolyl;

and n is zero or the integer one or two;

and the agronomically acceptable acid addition salts and metal salt complexes thereof.

2. A compound according to claim 1 wherein Z is a phenyl group optionally substituted with up to three substituents selected from the group consisting of halogen, ($C_1$-$C_4$)alkyl, ($C_1$-$C_4$)alkoxy, trihalomethyl, nitro and cyano.

3. A compound according to claim 2 wherein R is ($C_3$-$C_8$)alkyl, cyclohexyl, allyl, cyclohexenyl, propargyl, cyano, cyanomethyl, cyanoethyl, or a phenyl, phenoxy, phenoxy ($C_1$-$C_5$)alkyl, phenoxyphenyl ($C_1$-$C_5$)alkyl, phenylthio, phenylthio ($C_1$-$C_5$)alkyl and phenylthiophenyl ($C_1$-$C_5$)alkyl, the phenyl portions of which are optionally substituted with up to two substituents selected from the group consisting of halogen, ($C_1$-$C_4$)alkyl, ($C_1$-$C_4$)alkoxy, trihalomethyl, nitro and cyano.

4. A compound according to claim 2 wherein Z is a phenyl group optionally substituted with up to two halogen atoms; R is ($C_1$-$C_4$)alkyl, phenyl optionally substituted with up to two halogen atoms, phenoxy ($C_1$-$C_5$)alkyl the phenyl portion of which is optionally substituted with up to two halogen atoms; Azo is al imidazolyl or a 1(H) or 4(H)-1,2,4-triazolyl; and n is zero.

5. A compound according to claim 4 wherein Azo is a imidazolyl group.

6. A compound according to claim 5 wherein R is n-butyl, dihalosubstituted phenyl or dihalosubstituted phenoxy ($C_1$-$C_5$) alkyl.

7. A compound according to claim 1 having the formula

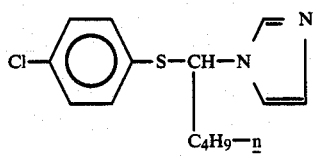

and the agronomically acceptable acid addition salts and metal salt complexes thereof.

8. A compound according to claim 1 having the formula

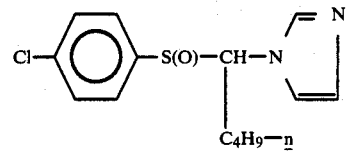

and the agronomically acceptable acid addition salts and metal salt complexes thereof.

9. A compound according to claim 1 having the formula

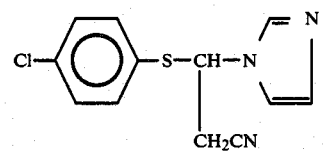

and the agronomically acceptable acid addition salts and metal salt complexes thereof.

10. A compound according to claim 1 having the formula

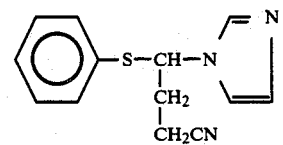

and the agronomically acceptable acid addition salts and metal salt complexes thereof.

11. A compound according to claim 1 having the formula

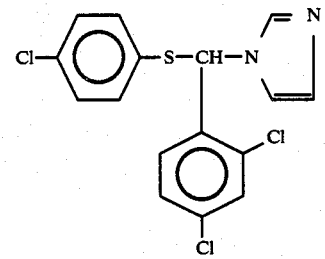

and the agronomically acceptable acid addition salts and metal salt complexes thereof.

12. A compound according to claim 1 having the formula

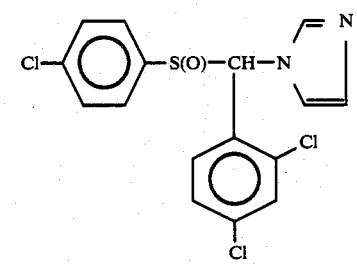

and the agronomically acceptable acid addition salts and metal salt complexes thereof.

13. A compound according to claim 1 having the formula

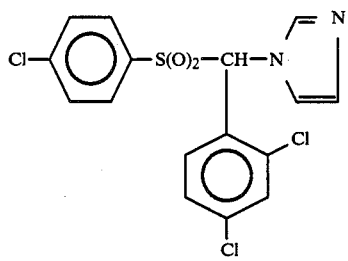

and the agronomically acceptable acid addition salts and metal salt complexes thereof.

14. A compound according to claim 1 having the formula

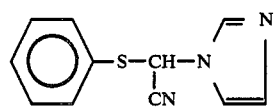

and the agronomically acceptable acid addition salts and metal salt complexes thereof.

15. A compound according to claim 1 having the formula

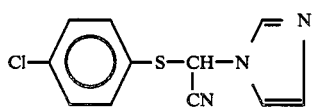

and the agronomically acceptable acid addition salts and metal salt complexes thereof.

16. A compound according to claim 1 having the formula

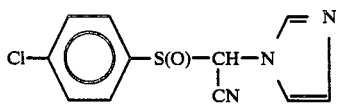

and the agronomically acceptable acid addition salts and metal salt complexes thereof.

17. A compound according to claim 1 having the formula

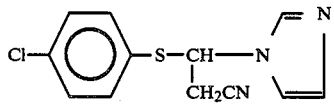

and the agronomically acceptable acid addition salts and metal salt complexes thereof.

18. A compound according to claim 1 having the formula

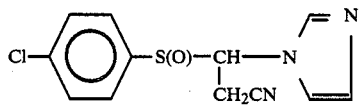

and the agronomically acceptable acid addition salts and metal salt complexes thereof.

19. A compound according to claim 1 having the formula

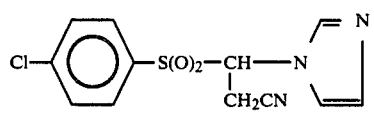

and the agronomically acceptable acid addition salts and metal salt complexes thereof.

20. A compound according to claim 1 having the formula

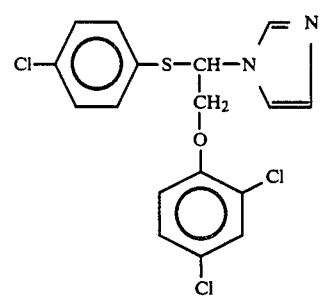

and the agronomically acceptable acid addition salts and metal salt complexes thereof.

21. A compound according to claim 1 having the formula

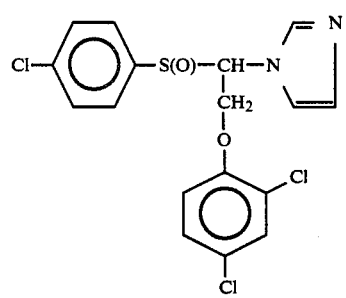

and the agronomically acceptable acid addition salts and metal salt complexes thereof.

22. A compound according to claim 1 having the formula

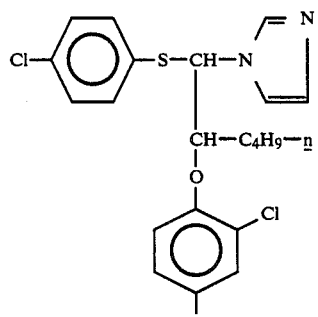

and the agronomically acceptable acid addition salts and metal salt complexes thereof.

23. A compound according to claim 1 having the formula

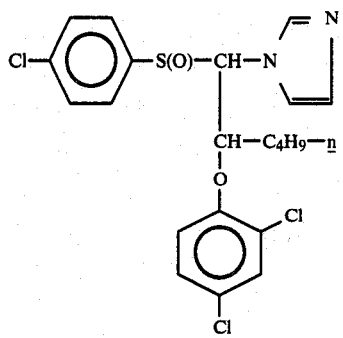

and the agronomically acceptable acid addition salts and metal salt complexes thereof.

24. A compound according to claim 1 having the formula

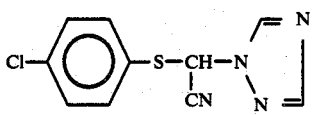

and the agronomically acceptable acid addition salts and metal salt complexes thereof.

25. A compound according to claim 1 having the formula

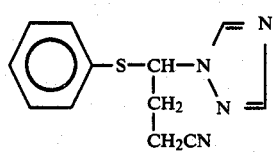

and the agronomically acceptable acid addition salts and metal salt complexes thereof.

26. A compound according to claim 1 having the formula

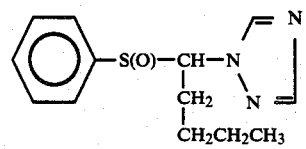

and the agronomically acceptable acid addition salts and metal salt complexes thereof.

27. A compound according to claim 1 having the formula

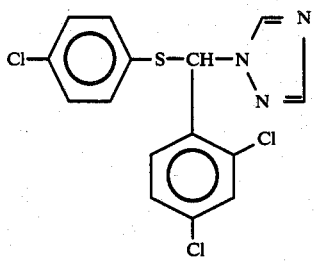

and the agronomically acceptable acid addition salts and metal salt complexes thereof.

28. A compound according to claim 1 having the formula

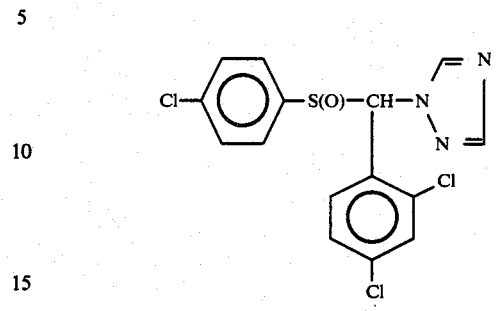

and the agronomically acceptable acid addition salts and metal salt complexes thereof.

29. A compound according to claim 1 having the formula

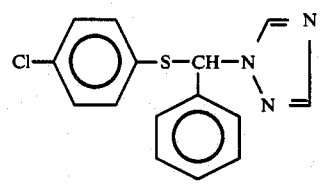

and the agronomically acceptable acid addition salts and metal salt complexes thereof.

30. A method for controlling phytopathogenic fungi which comprises applying to a plant, to plant seed or to a plant habitat, a fungicidally-effective amount of a compound according to the formula:

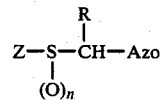

wherein

Z is a phenyl or naphthyl group optionally substituted with up to three substituents selected from the group consisting of halogen, $(C_1-C_4)$alkyl, $(C_1-C_4)$alkoxy, trihalomethyl, nitro and cyano;

R is
(a) $(C_1-C_{12})$ alkyl;
(b) $(C_3-C_8)$ cycloalkyl;
(c) $(C_2-C_8)$ alkenyl;
(d) $(C_5-C_8)$ cycloalkenyl;
(e) $(C_2-C_8)$ alkynyl;
(f) cyano;
(g) cyano $(C_1-C_4)$ alkyl;
(h) $(C_1-C_6)$ alkoxy $(C_1-C_6)$ alkyl;
(i) phenyl or naphthyl;
(j) phenoxy or naphthoxy;
(k) phenoxy $(C_1-C_9)$ alkyl or naphthyloxy $(C_1-C_9)$ alkyl;
(l) phenoxyphenyl $(C_1-C_9)$ alkyl, phenoxynaphthyl $(C_1-C_9)$ alkyl, naphthoxynaphthyl $(C_1-C_9)$ alkyl or naphthoxyphenyl $(C_1-C_9)$ alkyl;
(m) phenylthio or naphthylthio;
(n) phenylthio $(C_1-C_9)$ alkyl or naphthylthio $(C_1-C_9)$ alkyl; or
(o) phenylthiophenyl $(C_1-C_9)$ alkyl, phenylthionaphthyl $(C_1-C_9)$ alkyl, naphthylthiophenyl ($C_1$-$C_9$) alkyl or naphthylthionaphthyl ($C_1$-$C_9$) alkyl;

wherein when R is a substituent of (i), (j), (k), (l), (m), (n) or (o), the phenyl or naphthyl moiety of such substituent may be optionally substituted with up to three substituents selected from the group consisting of halogen, ($C_1$-$C_4$)alkyl, ($C_1$-$C_4$)alkoxy, trihalomethyl, nitro and cyano;

Azo is 1(H)-imidazolyl or 1(H)- or 4(H)-1,2,4-triazolyl;

and n is zero or the integer one or two;

and the agronomically acceptable acid addition salts and metal salt complexes thereof.

31. A fungicidal composition for controlling phytopathogenic fungi which comprises an agronomically acceptable carrier and as the active ingredient an effective amount of, a compound according to the formula

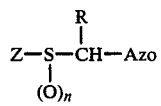

wherein

Z is a phenyl or naphthyl group optionally substituted with up to three substituents selected from the group consisting of halogen, ($C_1$-$C_4$)alkyl, ($C_1$-$C_4$)alkoxy, trihalomethyl, nitro and cyano;

R is
- (a) ($C_1$-$C_{12}$) alkyl;
- (b) ($C_3$-$C_8$) cycloalkyl;
- (c) ($C_2$-$C_8$) alkenyl;
- (d) ($C_5$-$C_8$) cycloalkenyl;
- (e) ($C_2$-$C_8$) alkynyl;
- (f) cyano;
- (g) cyano ($C_1$-$C_4$) alkyl;
- (h) ($C_1$-$C_6$) alkoxy ($C_1$-$C_6$) alkyl;
- (i) phenyl or naphthyl;
- (j) phenoxy or naphthoxy;
- (k) phenoxy ($C_1$-$C_9$) alkyl or naphthyloxy ($C_1$-$C_9$) alkyl;
- (l) phenoxyphenyl ($C_1$-$C_9$) alkyl, phenoxynaphthyl ($C_1$-$C_9$) alkyl, naphthoxynaphthyl ($C_1$-$C_9$) alkyl or naphthoxyphenyl ($C_1$-$C_9$) alkyl;
- (m) phenylthio or naphthylthio;
- (n) phenylthio ($C_1$-$C_9$) alkyl or naphthylthio ($C_1$-$C_9$) alkyl; or
- (o) phenylthiophenyl ($C_1$-$C_9$) alkyl, phenylthionaphthyl ($C_1$-$C_9$) alkyl, naphthylthiophenyl ($C_1$-$C_9$) alkyl or naphthylthionaphthyl ($C_1$-$C_9$) alkyl;

wherein when R is a substituent of (i), (j), (k), (l), (m), (n) or (o), the phenyl or naphthyl moiety of such substituent may be optionally substituted with up to three substituents selected from the group consisting of halogen, ($C_1$-$C_4$)alkyl, ($C_1$-$C_4$)alkoxy, trihalomethyl, nitro and cyano;

Azo is 1(H)-imidazolyl or 1(H)- or 4(H)-1,2,4-triazolyl;

and n is zero or the integer one or two;

and the agronomically acceptable acid addition salts and metal salt complexes thereof.

* * * * *